US012751814B2

(12) United States Patent
Nazer et al.

(10) Patent No.: US 12,751,814 B2
(45) Date of Patent: Oct. 6, 2026

(54) TRI-LEAFLET MECHANICAL HEART VALVE

(71) Applicant: KING SAUD UNIVERSITY, Riyadh (SA)

(72) Inventors: Rakan Ibrahim Nazer, Riyadh (SA); Ali Mufraih Albaratti, Riyadh (SA); Mohammed Abdullah Alshehri, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/032,246

(22) Filed: Jan. 20, 2025

(65) Prior Publication Data

US 2026/0207325 A1 Jul. 23, 2026

(51) Int. Cl.
*A61F 2/24* (2006.01)

(52) U.S. Cl.
CPC .... *A61F 2/2403* (2013.01); *A61F 2220/0033* (2013.01)

(58) Field of Classification Search
CPC ....................... A61F 2/2403; A61F 2220/0033
See application file for complete search history.

(56) References Cited

U.S. PATENT DOCUMENTS 5,192,309 A 3/1993 Stupka et al.
5,628,791 A 5/1997 Bokros et al.
5,824,062 A * 10/1998 Patke .................... A61F 2/2403 623/2.26
5,843,183 A 12/1998 Bokros et al.
6,896,700 B2 5/2005 Lu et al.
6,991,649 B2 * 1/2006 Sievers ................. A61F 2/2403 623/2.26
9,655,720 B2 * 5/2017 Bluestein .............. A61F 2/2418
10,478,288 B2 11/2019 Amerio et al.
2003/0114913 A1 * 6/2003 Spenser ................ A61F 2/2418 623/2.14
2005/0049697 A1 * 3/2005 Sievers ................. A61F 2/2403 623/2.31
2009/0118824 A1 5/2009 Samkov
2010/0185275 A1 * 7/2010 Richter ................. A61F 2/2412 623/2.11
2013/0046373 A1 * 2/2013 Cartledge ............... A61F 2/966 623/1.11

(Continued)

FOREIGN PATENT DOCUMENTS

CN 112190365 A * 1/2021 ........... A61F 2/2412

*Primary Examiner* — Suzette J Gherbi
(74) *Attorney, Agent, or Firm* — Nath, Goldberg & Meyer; Joshua B. Goldberg

(57) ABSTRACT

The tri-leaflet mechanical heart valve includes an annular valve base, a central post located at a center of the annular valve base, and first, second and third leaflets. Each of the first, second and third leaflets is pivotally attached to an inner surface of the annular valve base and pivotally attached to the central post. The first, second and third leaflets are equiangularly arranged within the annular valve base and each of the first, second and third leaflets has a twisted contour, similar to the twisted contour of a conventional fan blade or propellor blade. First, second and third stops may be mounted on the inner surface of the annular valve base to limit a degree of rotation of the first, second and third leaflets.

5 Claims, 9 Drawing Sheets

(56) References Cited

U.S. PATENT DOCUMENTS

| | | | | |
|---|---|---|---|---|
| 2014/0172080 | A1* | 6/2014 | Bruchman | A61F 2/2415 156/185 |
| 2017/0086969 | A1* | 3/2017 | Amerio | A61F 2/2403 |
| 2017/0245989 | A1* | 8/2017 | Bluestein | A61F 2/2418 |
| 2021/0030535 | A1* | 2/2021 | Liu | A61F 2/2418 |
| 2021/0212821 | A1* | 7/2021 | Perrier | A61F 2/2403 |
| 2021/0259833 | A1* | 8/2021 | Maimon | A61F 2/2409 |
| 2023/0110800 | A1* | 4/2023 | Dienno | A61F 2/2439 623/2.11 |
| 2024/0058117 | A1* | 2/2024 | Ali | A61F 2/2403 |
| 2024/0065830 | A1* | 2/2024 | Cohen | A61F 2/2403 |
| 2024/0081996 | A1* | 3/2024 | Uong | A61F 2/2445 |
| 2025/0009499 | A1* | 1/2025 | Schwartz | A61F 2/2412 |

* cited by examiner

TRI-LEAFLET MECHANICAL HEART VALVE

BACKGROUND

Field

The disclosure of the present patent application relates to mechanical heart valves, and particularly to a tri-leaflet mechanical heart valve with twisted, propellor or fan blade-like leaflets.

Description of Related Art

Heart valve replacement surgery is one of the most effective therapies for valvular diseases. Generally, there are two major types of artificial heart valves. The first type is the Mechanical Heart Valve (MHV), which is completely composed of artificial materials. The second type is the Bioprosthetic Heart Valve (BHV), which consists of chemically treated biomaterials. The MHV essentially includes one or more leaflets, an annular valve base, a hinge and a sewing ring. The leaflets are occluders for the opening and closing of the valve, which operates 0-200 times every minute inside the human body. The valve base serves as a frame for holding the occluders. The hinge rotatably supports the leaflets in the valve base. The sewing ring is a woven material surrounding the MHV for attachment to the implantation site.

Bi-leaflet heart valves form three streams when the two leaflets are opened, which is non-symmetric with respect to a center of the heart valve. Non-hermetic compliance with the aortic sinuses leads to a non-symmetric flow profile, thus inducing a large velocity gradient and turbulence. Since the bi-leaflet MHV is centrally asymmetric, the two leaflets are not opened synchronously, leading to great recirculation of blood and increasing the burden of heart. To overcome such deficiencies, tri-leaflet heart valves are of great interest.

Hemodynamically, the tri-leaflet heart valve opens to form a single central flow, similar to the operation of the human aortic valve. The pressure induced by the circulation of blood inside semi-circular aortic sinuses downstream from the heart valve helps to open and close the heart valve. The most important factors in the design of the tri-leaflet heart valve are the shape of the leaflets and the pivoting mechanism.

FIGS. 2A and 2B illustrate a conventional tri-leaflet heart valve 100. The heart valve 100 includes an annular valve base 121, three leaflets 122 and three hinges 130 formed on the inner surface of the annular valve base 121 in an equally spaced manner for rotatably mounting the leaflets 122. The leaflets 122 are allowed to rotate freely with respect to the annular valve base 121 for opening and closing the heart valve 100. The heart valve 100 functions as a one-way valve by means of which blood is allowed to flow from the upstream side to the downstream side of the valve 100, but not in the opposite direction. Stagnation and turbulence in blood flow are generally avoided when the blood is flowing through the valve in order to reduce thrombosis and hemolysis.

Each leaflet 122 is positioned between adjacent hinges 130. Each leaflet 122 has round pivots 140 on both sides rotatably received in, and supported by, concave sockets of the adjacent protruding hinge 130. Rotation of the leaflet 122 with respect to the annular valve base 121 about the pivots 140 thereby opens and closes the heart valve 100. In conventional heart valve 100, each leaflet 122 forms a triangle with two side edges 145 extending from an apex 147 that points downstream, and a curved bottom edge which forms a mating face. The side edges 145 are configured so that, when the heart valve 100 is closed, the side edges 145 of adjacent leaflets 122 tightly engage each other, while the mating face of the bottom edge contacts a curved recess to occlude the heart valve 100. Each leaflet 122 has a concave inner surface 142 and a convex outer surface 143.

Although versatile and in wide use, conventional mechanical heart valves, such as those discussed above, result in hemodynamics which are not fully compatible with the natural "swirling" of blood as it is ejected from the heart. Thus, a tri-leaflet mechanical heart valve solving the aforementioned problems is desired.

SUMMARY

The tri-leaflet mechanical heart valve includes an annular valve base, a central post located at a center of the annular valve base, and first, second and third leaflets. Each of the first, second and third leaflets is pivotally attached to an inner surface of the annular valve base and pivotally attached to the central post. The first, second and third leaflets are equiangularly arranged within the annular valve base and each of the first, second and third leaflets has a twisted contour, similar to the twisted contour of a conventional fan blade or propeller blade, as non-limiting examples. First, second and third stops may be mounted on the inner surface of the annular valve base to limit a degree of rotation of the first, second and third leaflets.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
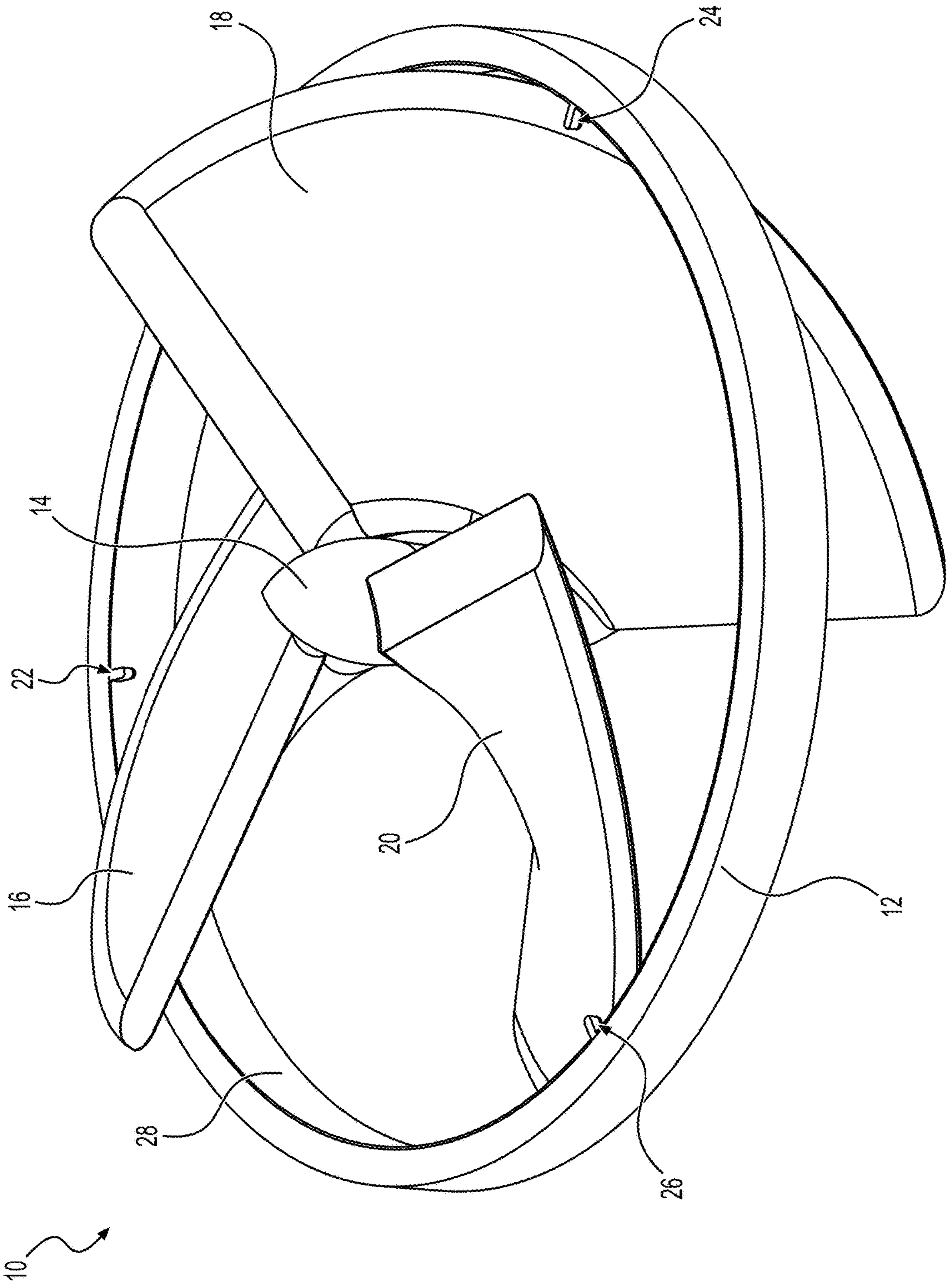
FIG. 1 is a perspective view of a tri-leaflet mechanical heart valve.
Figure 2A:
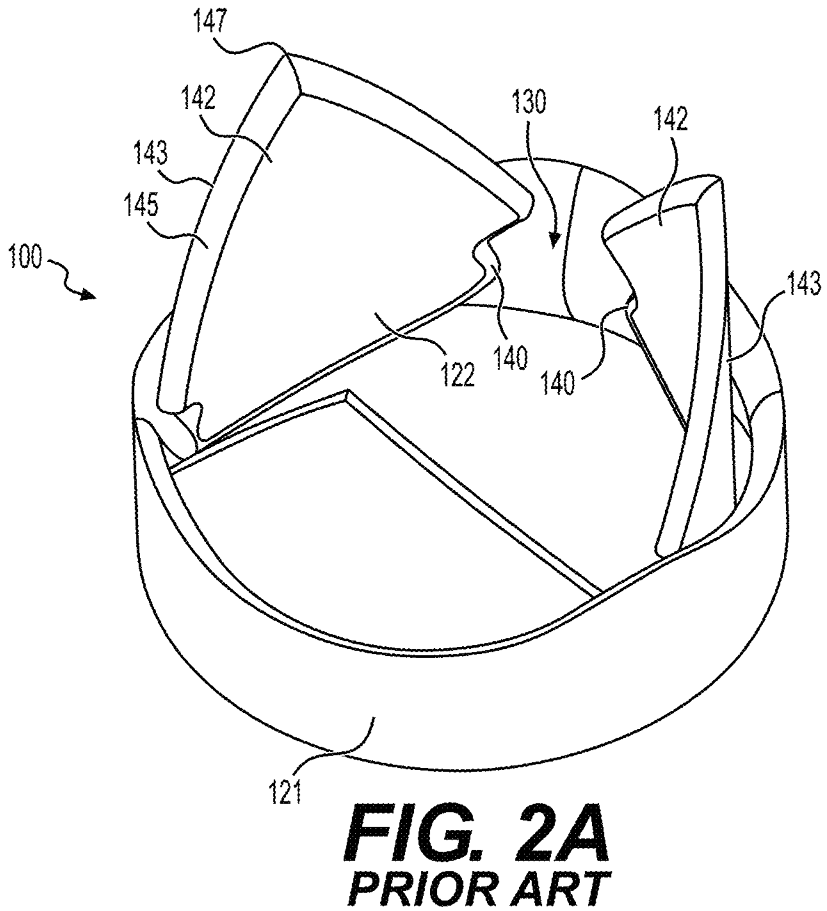
FIG. 2A PRIOR ART
FIG. 2A is a perspective view of a conventional mechanical heart valve shown in an open configuration.
Figure 2B:
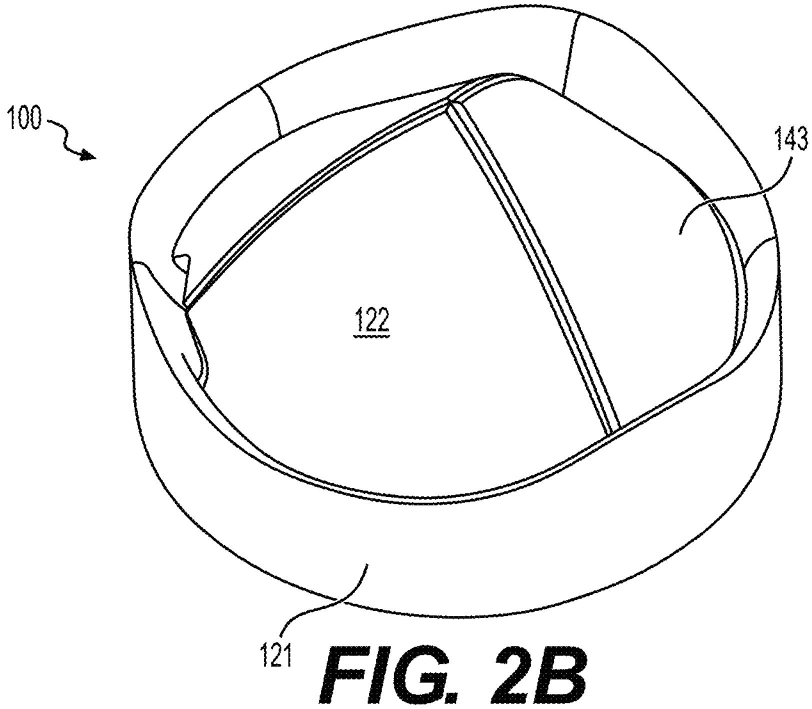
FIG. 2B PRIOR ART
FIG. 2B is a perspective view of the conventional mechanical heart valve shown in a closed configuration.

The tri-leaflet mechanical heart valve 10 includes an annular valve base 12, a central post 14 located at a center of the annular valve base 12, and first, second and third leaflets 16, 18 and 20, respectively. Each of the first, second and third leaflets 16, 18 and 20 is pivotally attached to an inner surface 28 of the annular valve base 12 and pivotally attached to the central post 14. It should be understood that the relative dimensions of the annular valve base 12 are shown for exemplary purposes only and may be varied. It should be similarly understood that the overall shape and relative dimensions of the central post 14 are shown for exemplary purposes only and may be varied.

The first, second and third leaflets 16, 18 and 20 are equiangularly arranged within the annular valve base 12. As shown, the first, second and third leaflets 16, 18 and 20 may each have a shape approximating a third of a circle, but each of the first, second and third leaflets 16, 18 and 20 has a twisted contour, similar to the twisted contour of a conventional fan blade or propellor blade, as non-limiting examples.

Figure 3A:
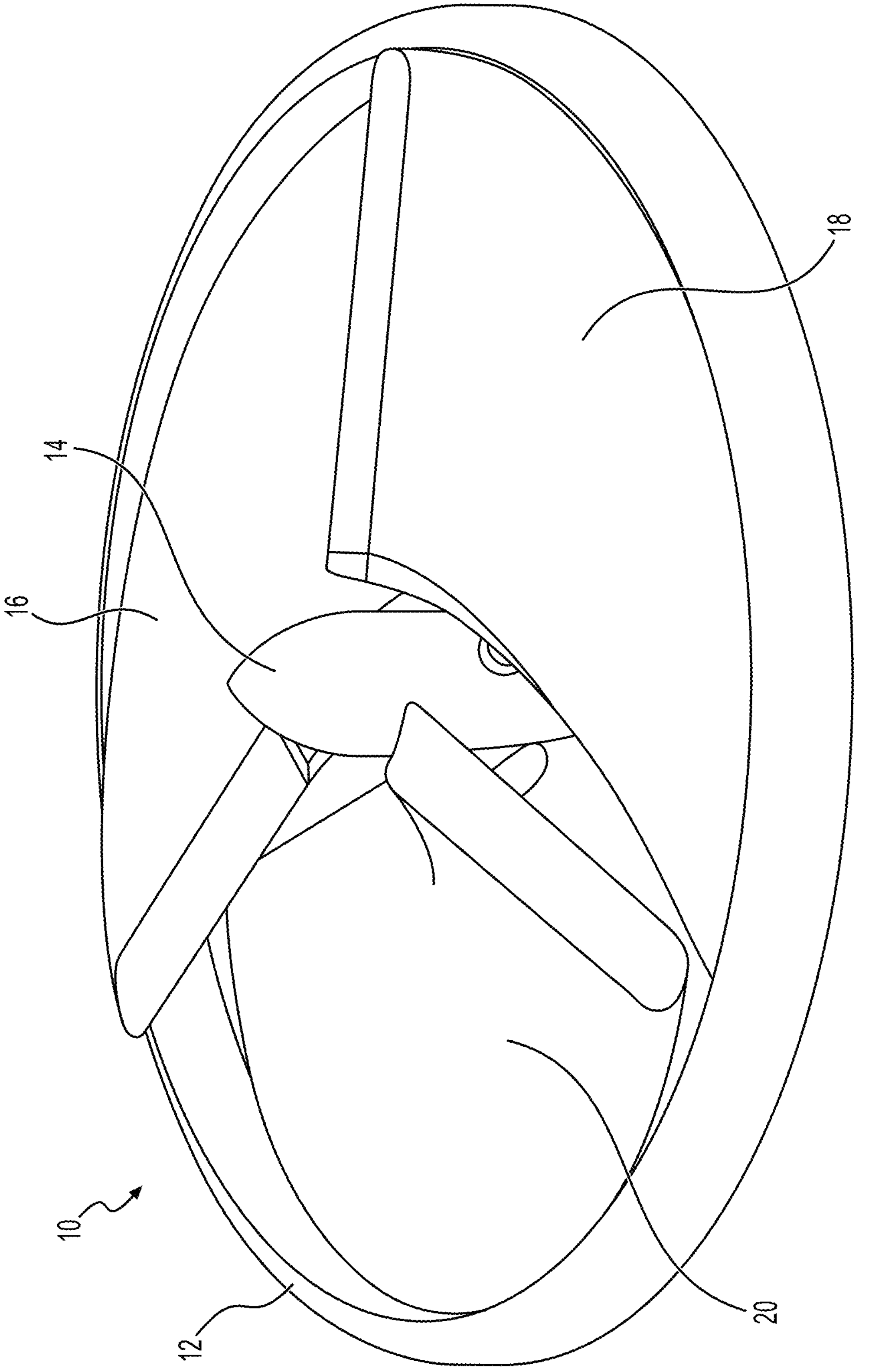
FIGS. 3A, 3B, 3C, 3D and 3E are perspective views of the tri-leaflet mechanical heart valve, illustrating the tri-leaflet mechanical heart valve moving through a full cycle of opening and closing.
Figure 3B:
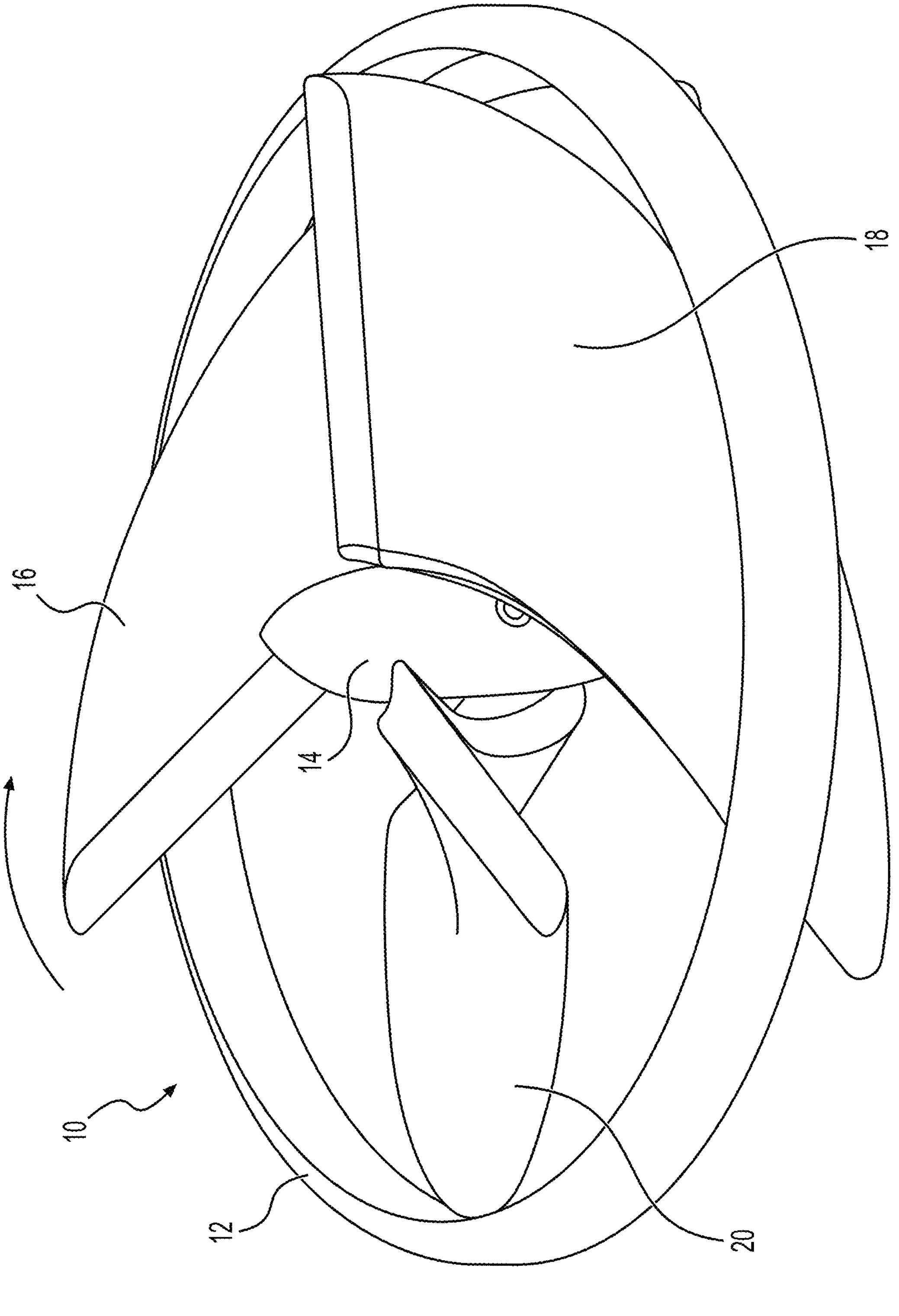
Figure 3C:
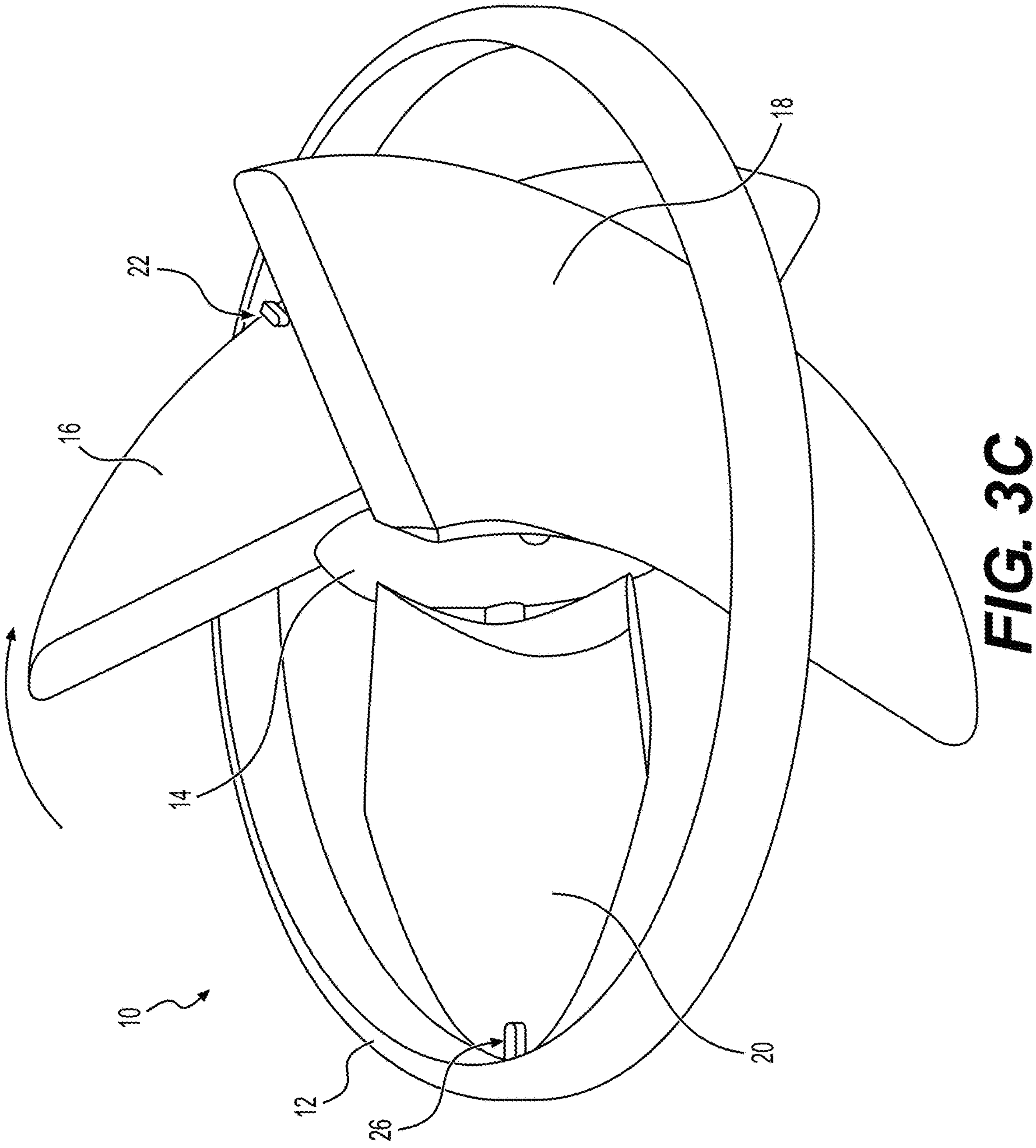
Figure 3D:
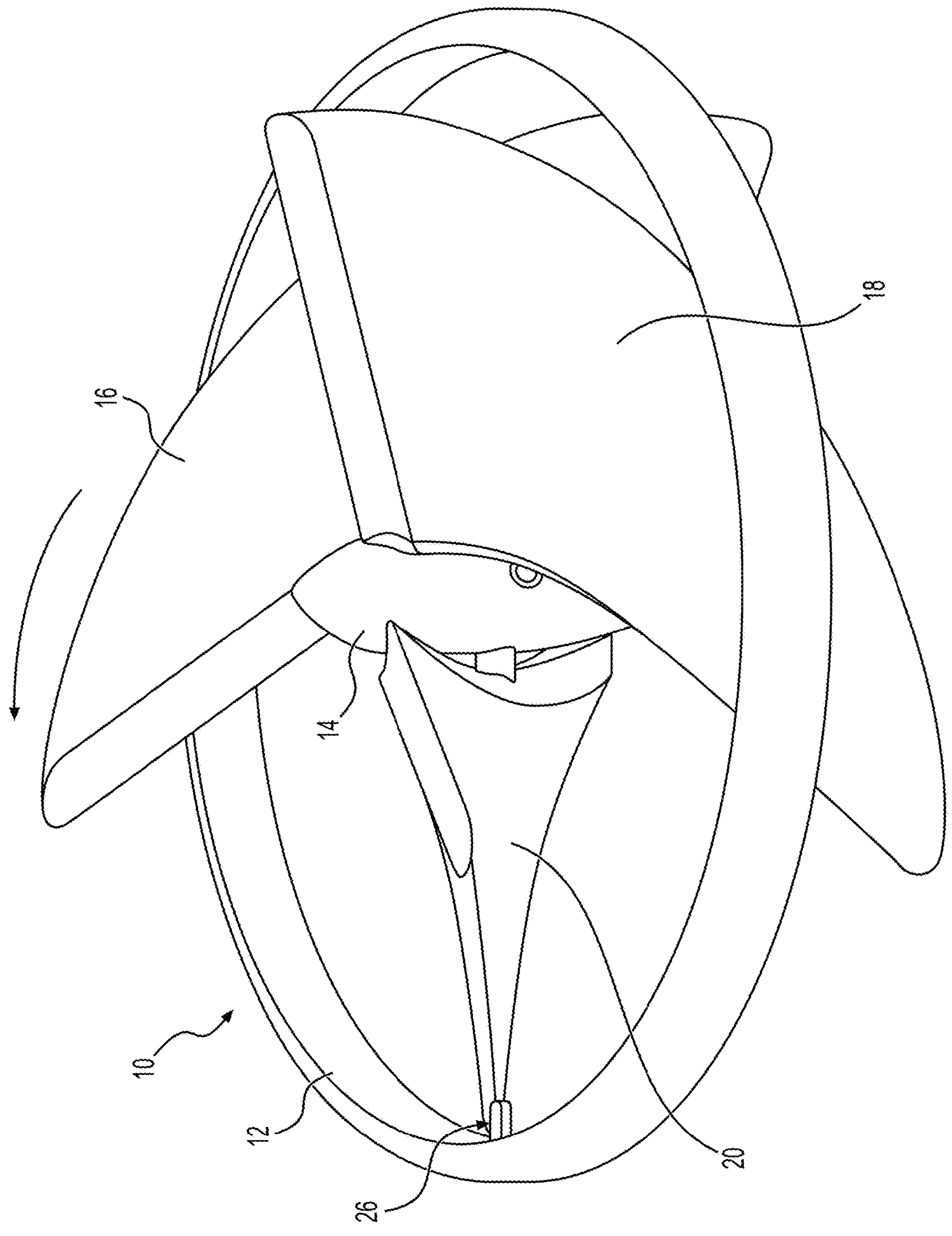
Figure 3E:
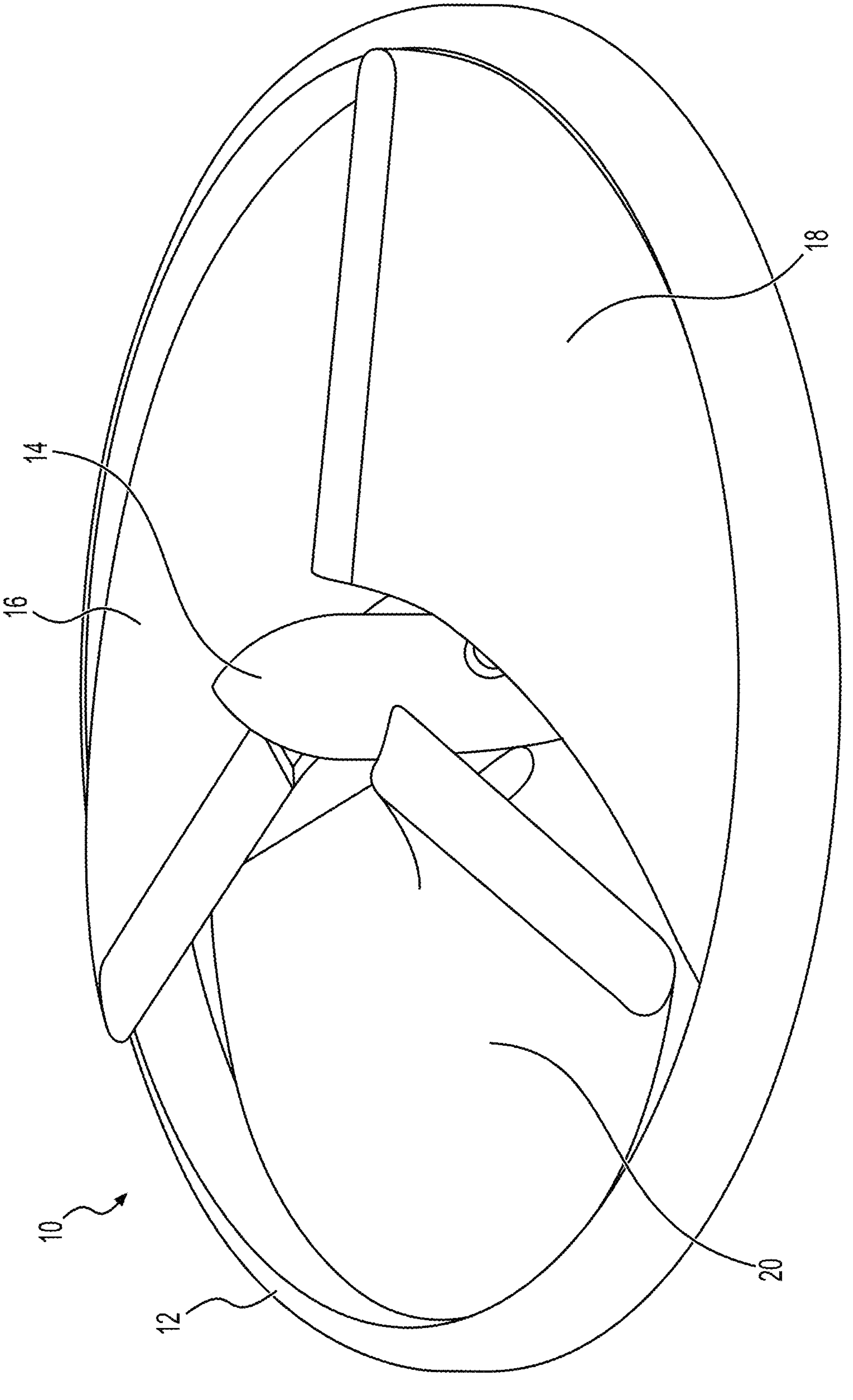

First, second and third stops 22, 24 and 26, respectively, may be mounted on the inner surface 28 of the annular valve base 12 to limit a degree of rotation of the first, second and third leaflets 16, 18 and 20, respectively. As shown in FIGS. 3A and 3B, in use, the valve 10 moves from a closed configuration into the open configuration by rotation of each of the first, second and third leaflets 16, 18 and 20 with respect to both the central post 14 and the annular valve base 12. For purposes of clarity, only rotation of the first leaflet 16 is indicated in FIG. 3B with an arrow, although it should be understood that each of the first, second and third leaflets 16, 18 and 20 is rotating simultaneously. As shown in FIG. 3C, rotation continues until the first, second and third leaflets 16, 18 and 20 are stopped by the first, second and third stops 22, 24 and 26, respectively. At this point, the valve 10 is in the fully open configuration. For purposes of clarity, only the first and third stops 22 and 26 are indicated in FIG. 3C, although it should be understood that each of the first, second and third leaflets 16, 18 and 20 is stopped at the same angle and at the same time by the first, second and third stops 22, 24 and 26, respectively. As indicated in FIGS. 3D and 3E, in order to close the valve 10, the first, second and third leaflets 16, 18 and 20 each rotate simultaneously in the reverse direction. Each of the first, second and third leaflets 16, 18 and 20 rotates through a span of approximately 90°.

Figure 4:
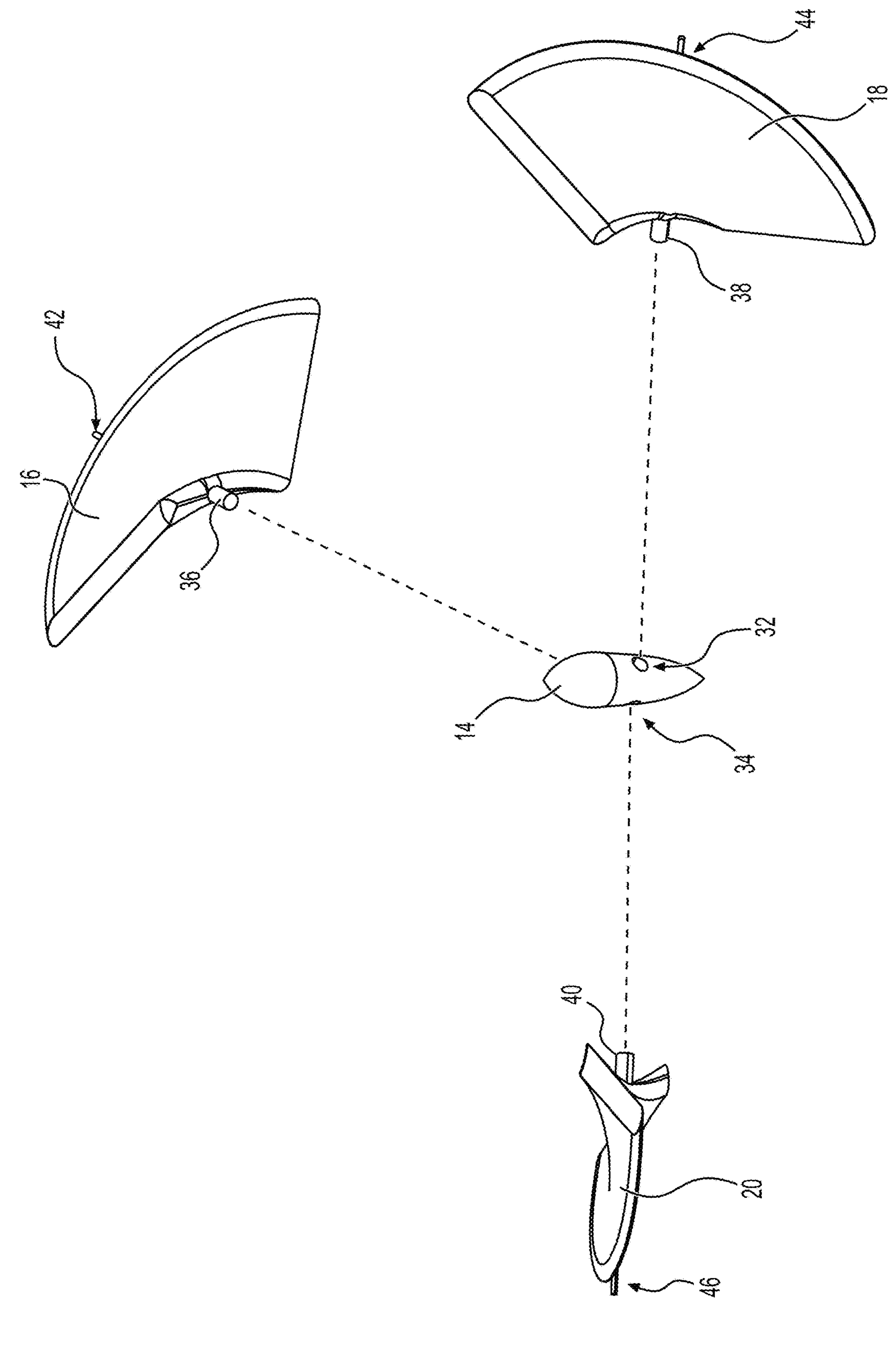
FIG. 4 is a perspective, exploded view of a central post and first, second and third leaflets of the tri-leaflet mechanical heart valve.
Figure 5:
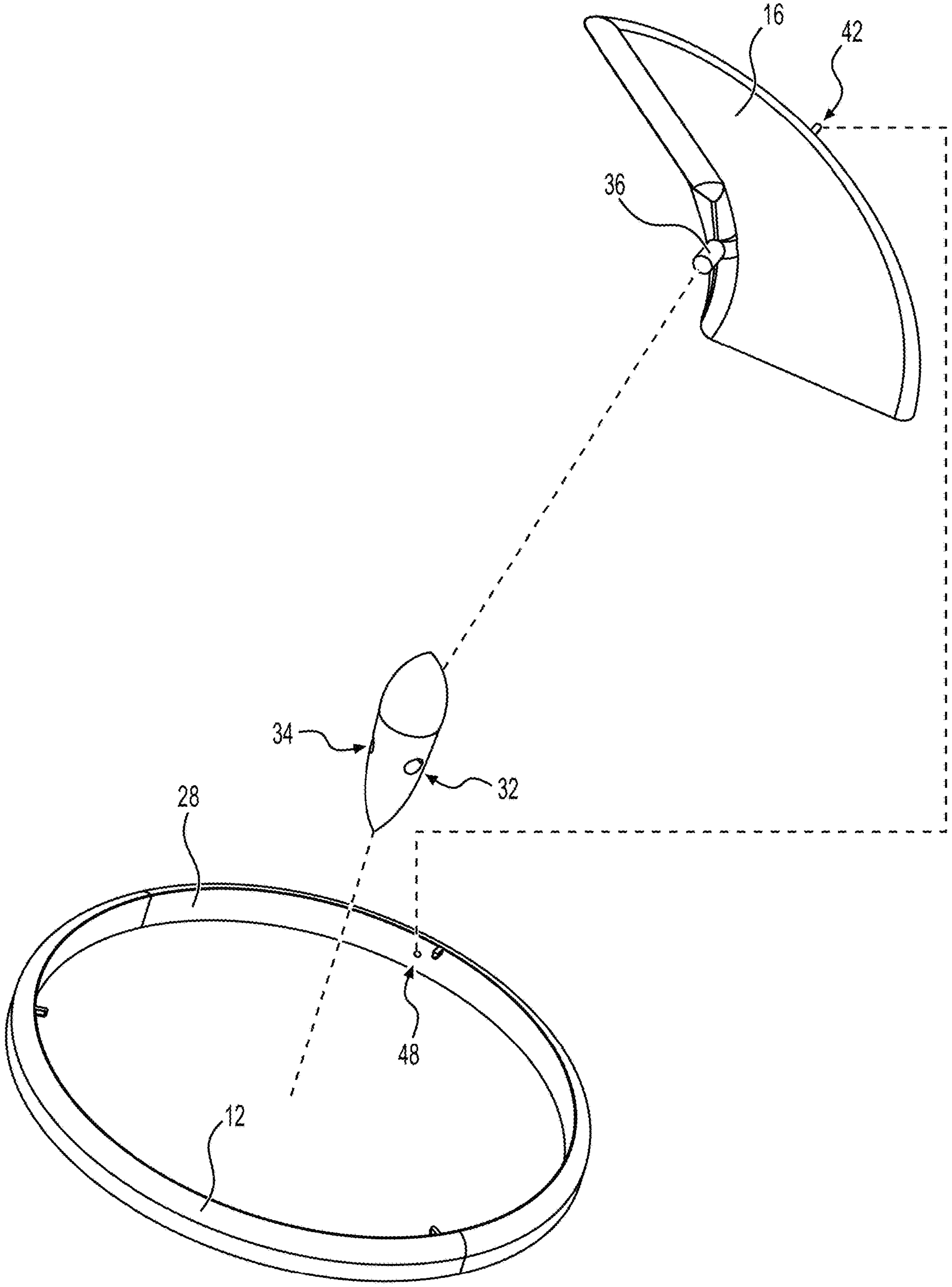
FIG. 5 is a partial perspective, exploded view of the tri-leaflet mechanical heart valve.

It should be understood that the first, second and third leaflets 16, 18 and 20 may be pivotally attached to the inner surface 28 and to the central post 14 using any suitable type of pivotal connection. In the non-limiting example of FIG. 4, each of the first, second and third leaflets 16, 18 and 20 has an inner engaging member 36, 38 and 40, respectively, and an outer engaging member 42, 44 and 46, respectively. The central post 14 has first, second and third post recesses formed therein for respectively rotatably receiving the inner engaging members 36, 38 and 40 of the first, second and third leaflets 16, 18 and 20. In FIG. 4, only the second and third post recesses 32 and 34, respectively, can be seen, however, it should be understood that the first post recess is also formed in central post 14. The first, second and third post recesses are equiangularly arranged about central post 14. Additionally, the inner surface 28 of the annular valve base 12 has first, second and third base recesses formed therein for respectively rotatably receiving the outer engaging members 42, 44 and 46, respectively, of the first, second and third leaflets 16, 18 and 20. For purposes of clarity, FIG. 5 only shows the first base recess 48, however, it should be understood that the second and third base recesses are provided in the inner surface 28 for receiving the second and third outer engaging members 44 and 46, respectively.

It is to be understood that the tri-leaflet mechanical heart valve is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

The invention claimed is:

1. A tri-leaflet mechanical heart valve, comprising:

an annular valve base;

a central post located at a center of the annular valve base; and first, second, and third leaflets, wherein each of the first, second, and third leaflets is pivotally attached to an inner surface of the annular valve base and pivotally attached to the central post.

2. The tri-leaflet mechanical heart valve as recited in claim 1, wherein each of the first, second, and third leaflets has a twisted contour.

3. The tri-leaflet mechanical heart valve as recited in claim 1, further comprising first, second, and third stops mounted on the inner surface of the annular valve base to limit a degree of rotation of the first, second, and third leaflets.

4. The tri-leaflet mechanical heart valve as recited in claim 1, wherein each of the first, second, and third leaflets has an inner engaging member and an outer engaging member, wherein the central post has first, second, and third post recesses formed therein for respectively rotatably receiving the inner engaging members of the first, second, and third leaflets, and wherein the inner surface of the annular valve base has first, second, and third base recesses formed therein for respectively rotatably receiving the outer engaging members of the first, second, and third leaflets.

5. The tri-leaflet mechanical heart valve as recited in claim 1, wherein the first, second, and third leaflets are equiangularly arranged within the annular valve base.

* * * * *